United States Patent
Gibson et al.

(10) Patent No.: US 9,216,477 B2
(45) Date of Patent: Dec. 22, 2015

(54) AMPOULE LABELS

(71) Applicant: Holitas Limited, Hitchin (GB)

(72) Inventors: Mark Gibson, Hitchin Herts (GB); Peter Ernest Tasko, Hitchin (GB)

(73) Assignee: Holitas Limited, Hitchin (GB)

( * ) Notice: Subject to any disclaimer, the term of this patent is extended or adjusted under 35 U.S.C. 154(b) by 66 days.

(21) Appl. No.: 13/966,449

(22) Filed: Aug. 14, 2013

(65) Prior Publication Data

US 2014/0048066 A1    Feb. 20, 2014

(30) Foreign Application Priority Data

Aug. 16, 2012  (GB) .................................. 1214643.7

(51) Int. Cl.
| B29C 65/00 | (2006.01) |
| B23K 26/36 | (2014.01) |
| G09F 3/10 | (2006.01) |
| G09F 7/16 | (2006.01) |
| A61M 15/00 | (2006.01) |

(52) U.S. Cl.
CPC ............... *B23K 26/365* (2013.01); *G09F 3/10* (2013.01); *G09F 7/165* (2013.01); *A61J 2205/30* (2013.01); *A61M 15/0028* (2013.01); *A61M 2205/6072* (2013.01); *Y10T 428/12389* (2015.01); *Y10T 428/12396* (2015.01); *Y10T 428/24612* (2015.01); *Y10T 428/24802* (2015.01)

(58) Field of Classification Search
CPC ........... B23K 26/365; A61M 15/0028; A61M 2205/6072; A61J 2205/30; G09F 3/10; G09F 7/165; Y10T 428/12396; Y10T 428/24802; Y10T 428/24612; Y10T 428/12389
USPC .......................... 156/277, 272.8; 128/203.21; 219/121.69; 428/172, 195.1, 600, 601
See application file for complete search history.

(56) References Cited

U.S. PATENT DOCUMENTS

| 2004/0048172 A1 | 3/2004 | Fischer |
| 2008/0192107 A1 | 8/2008 | Griffin et al. |
| 2011/0256391 A1 * | 10/2011 | Nguyen et al. ................ 428/343 |

FOREIGN PATENT DOCUMENTS

| JP | 2006220695 | 8/2006 |
| WO | 2006085063 | 8/2006 |
| WO | 2007032900 | 3/2007 |

* cited by examiner

*Primary Examiner* — Jacob T Minskey
*Assistant Examiner* — Vishal I Patel
(74) *Attorney, Agent, or Firm* — K&L Gates LLP

(57) ABSTRACT

Nebulizer ampoules are labelled by laser-marking or laser-engraving data on a film to produce a data film and affixing the film onto a nebulizer ampoule using a non-migratory adhesive.

9 Claims, 4 Drawing Sheets

AMPOULE LABELS

INCORPORATION BY REFERENCE

Figure 1:
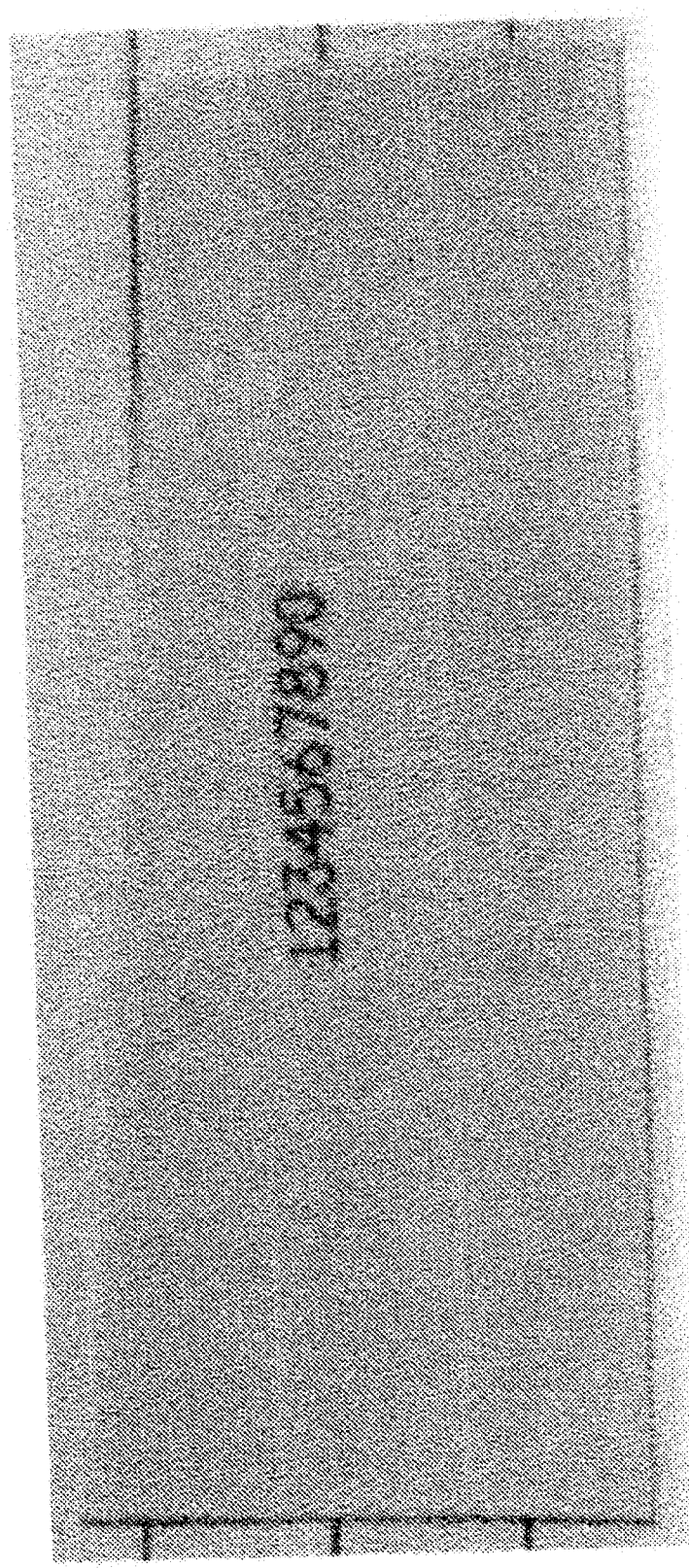

This application is based upon and claims the benefit of priority from corresponding Great Britain Patent Application No. 1214643.7, filed on Aug. 16, 2012, the entire contents of which are incorporated herein by reference.

BACKGROUND

The present invention relates to a method for labelling nebuliser ampoules manufactured using Blow Fill and Seal or Form Fill technology wherein the enclosed medicament is intended for delivery via the inhalation route.

Small molecules present in paper, adhesive and printing ink, such as the ink used in laser, inkjet or impact printing, can migrate through labels and polymer ampoule walls. This is a particular problem, for example, with nebulizer products made from low density polymers according to blow-fill-seal or form-fill-seal methods. The migration of these small molecules is considered a health and safety issue for nebulizer ampoules because the contents are medicaments intended for inhalation, and it is thought that components that migrate into the ampoule may incorporate potentially hazardous material into the medicament contained therein. Accordingly, for example, the United States Food and Drug Administration (US FDA) does not at present accept ink-based labelling for blow-fill-seal nebulizer ampoules intended for the inhalation route of administration.

However, there remains a need for alternative labelling of nebulized product ampoules. A current solution is to label nebulized product ampoules by embossing. However, embossing is an expensive and time consuming process. The process involves machining the moulding tooling with the desired labelling so that molten polymer can be drawn into the machined moulding inserts to leave the required embossed labelling on the surface of the product container. Each product needs a unique set of tooling and each time a different product requires manufacture, a different set of uniquely machined tooling needs to be fitted. Tooling is expensive and changing tooling on modern BFS machines causes extensive downtime.

As general background, JP 2006/220695 discloses a label for medical packaging comprising a protective layer of a colour different from a transparent print layer. WO2007/032900 describes a multi-layer laminate media, on which information may be applied in machine or human readable form using lasers or other high intensity light sources. US2004/0048172 describes a label film that can be inscribed using a laser beam. US2011/0256391 describes a layered material comprising polyvinylbutyral and an adhesive, wherein the polyvinylbutyral layer comprises irradiation-treated areas for use as a label.

SUMMARY

The present invention seeks to provide alternative labelling of ampoules and in embodiments seeks to overcome one or more of these problems by providing a fast and inexpensive ampoule labelling method, which produces labels that comply with the US FDA regulations and/or otherwise allays health and safety concerns regarding labelling of ampoules containing medicaments for the inhalation route of administration.

Accordingly, the invention provides a method of labelling a nebulizer ampoule comprising (i) laser-marking or laser-engraving data on a film to produce a data film and (ii) affixing the film onto a nebulizer ampoule using a non-migratory adhesive.

Additional features and advantages are described herein, and will be apparent from the following Detailed Description and the figures.

BRIEF DESCRIPTION OF THE FIGURES

The invention is now illustrated in more detail in the following specific embodiments, with reference to the attached drawings in which:

FIG. 1 shows a polypropylene-on-aluminium label of the invention;

FIG. 2 shows a further polypropylene-on-aluminium label of the invention;

FIG. 3 shows a polyethylene/water based acrylic adhesive/aluminium label of the invention; and FIG. 4 shows a further polyethylene/water based acrylic adhesive/aluminium label of the invention.

DETAILED DESCRIPTION

Laser-marking and laser-etching involves scanning across the film a laser beam of sufficient power to modify the surface to form data thereon, e.g. an image comprising text and/or other graphics. In the case of laser-marking, the film is generally darkened, preferably blackened, by the laser. In the case of laser-etching, the laser generally forms grooves or pits in the film. In the invention, the laser generally does not create full-thickness holes in the film. The laser may be driven by and produce a rasterized image, or it may be driven by vector graphics to plot text and/or other graphics.

In the context of the invention, the terms laser-marking and laser-engraving refer to technology that marks substrates without the use of inks. This contrasts with the use in common laser printing of toner comprising ink and/or other potentially harmful compounds, in which a laser is used to charge a photoreceptor (e.g. paper) to attract toner particles.

Thus, the invention advantageously provides a method that uses no ink and hence eradicates the risk of ink components migrating into a nebulizer ampoule and mixing with medicament contained therein. The use of laser-marking or laser-etching advantageously provides a fast, non-contact and hence hygienic labelling method.

Moreover, the process allows for offline printing of labels so that for common sizes of ampoules, no tooling changes are required as a result of a need to change the product labelling to be attached to an ampoule. Additionally, the costs for changing parts is greatly reduced as common tooling sets can be used for multiple products.

Suitable lasers include ultraviolet (UV) gas, diode or solid-state lasers, or neodymium-doped yttrium aluminium garnet (Nd:YAG) lasers. Other suitable lasers are known to the skilled person.

UV lasers can provide a small illumination spot due to their short wavelength emission, and so can typically provide higher resolution marking or etching than Nd:YAG lasers. UV lasers may thus be more capable of producing small print, which is advantageous when marking labels for small volume (e.g. less than 5 ml) nebulizer ampoules. UV lasers are also usually more powerful than Nd:YAG lasers, which allows for more rapid labelling. However, where marking resolution and/or speed is less important, Nd:YAG lasers can provide a suitable labelling means at lower cost than UV lasers.

In a preferred embodiment, the method of the invention comprises laser-marking or laser-engraving data on a film to produce a data film and then affixing the film onto a nebulizer ampoule using a non-migratory adhesive. This has the advantage of enabling labels to be produced and marked in bulk in a specialised machine before affixing to nebulizer ampoules.

In an alternative embodiment, the method of the invention comprises affixing a film onto a nebulizer ampoule using a non-migratory adhesive then laser-marking or laser-engraving data on the film to produce a data film. This has the advantage of providing greater flexibility for the contents of a label, thus enabling the information on the label to be changed on a single ampoule to ampoule basis. This option may be of particular benefit in the context of personalized medicine.

In the invention, the laser-engraving or laser-marking generally does not produce holes that penetrate the full thickness of the data film.

In embodiments of the invention, the data film comprises a plastic film or metal foil, preferably a plastic film, more preferably a film of polyester, polypropylene or polyethylene. The plastic may optionally be a copolymer. Plastic films are advantageously inexpensive and convenient to produce and enable the inclusion of additives to enhance contrast. For example, the data film may incorporate titanium dioxide to whiten the plastic, or a dye to colour the plastic. The film is preferably opaque to enhance contrast between the marking/etching and the film, and to guide the eye of the user of the ampoule to the label and to the important information contained thereon. In addition, thin plastic films are structurally flexible and so less likely to peel off if the underlying ampoule is flexed or deformed. Specific embodiments of the invention comprise a filled or dyed polymer film, to be adhered by adhesive onto an ampoule.

The metal foil preferably comprises aluminium. Aluminium is a relatively inexpensive and malleable metal. Metal foils are particularly suitable for applications that require a stronger rigidity to that of a plastic film of similar thickness.

In an embodiment of the invention, an intermediate film is located between the data film and the non-migratory adhesive. The intermediate film is preferably opaque. The intermediate film can provide an additional barrier between the labelled surface of the data film and the ampoule. The data film may be affixed onto the intermediate film using standard or non-migratory adhesive; the use of standard water based adhesive between the data film and the intermediate film in this embodiment is possible because the material of the intermediate film may be selected to be impermeable such that adhesive does not migrate through the intermediate film and thus the adhesive does not come into contact with the ampoule wall.

The intermediate film may be plastic or metal, preferably a metal foil, more preferably an aluminium foil. Hence in certain embodiments, a data film in combination with a foil is used to increase contrast and improve the labelling clarity.

In further embodiments of the invention, first and second intermediate films are located between the data film and the non-migratory adhesive. Each of the first and second intermediate films can independently be a metal or plastic film. In one arrangement, the data film is plastic, the first intermediate film is a foil, e.g. aluminium and the second is plastic—both plastic films may independently be polyester, polypropylene or polyethylene.

Further specific embodiments of the invention include (i) polymer film directly adhered to a metal film, which metal film is to be attached to an ampoule using adhesive, and (ii) polymer film attached via adhesive to a metal film, which metal film is to be attached to an ampoule using adhesive.

The non-migratory adhesive may be any suitable non-migratory adhesive known to the skilled person. Preferably, the non-migratory adhesive is waterborne and acrylic-based. An example of suitable non-migratory adhesive is UPM Raflatac® RP 31 Purus (also known as RP 31 C).

Accordingly, by combining suitable film materials and adhesives, the invention advantageously provides a method that reduces the risk of contaminants, e.g. inks, migrating into a nebulizer ampoule and mixing with medicament contained therein.

The labelling method of the invention is particularly suitable for nebulizer ampoules made from low density polypropylene or polyethylene by blow-fill-seal methods containing e.g. 5 ml or less medicament.

Direct laser marking of clear nebulizer ampoules has been found to be unsatisfactory. Therefore, the use of a markable data film advantageously enables labelling of ampoules using laser-marking or laser-etching.

An alternative aspect of the invention provides a nebulizer ampoule label comprising a laser-marked or laser-engraved data film and a non-migratory adhesive. In a further alternative aspect, the invention provides a nebulizer ampoule comprising a label of the invention. These aspects are suitably made by methods of the invention.

EXAMPLE 1

Figure 2:
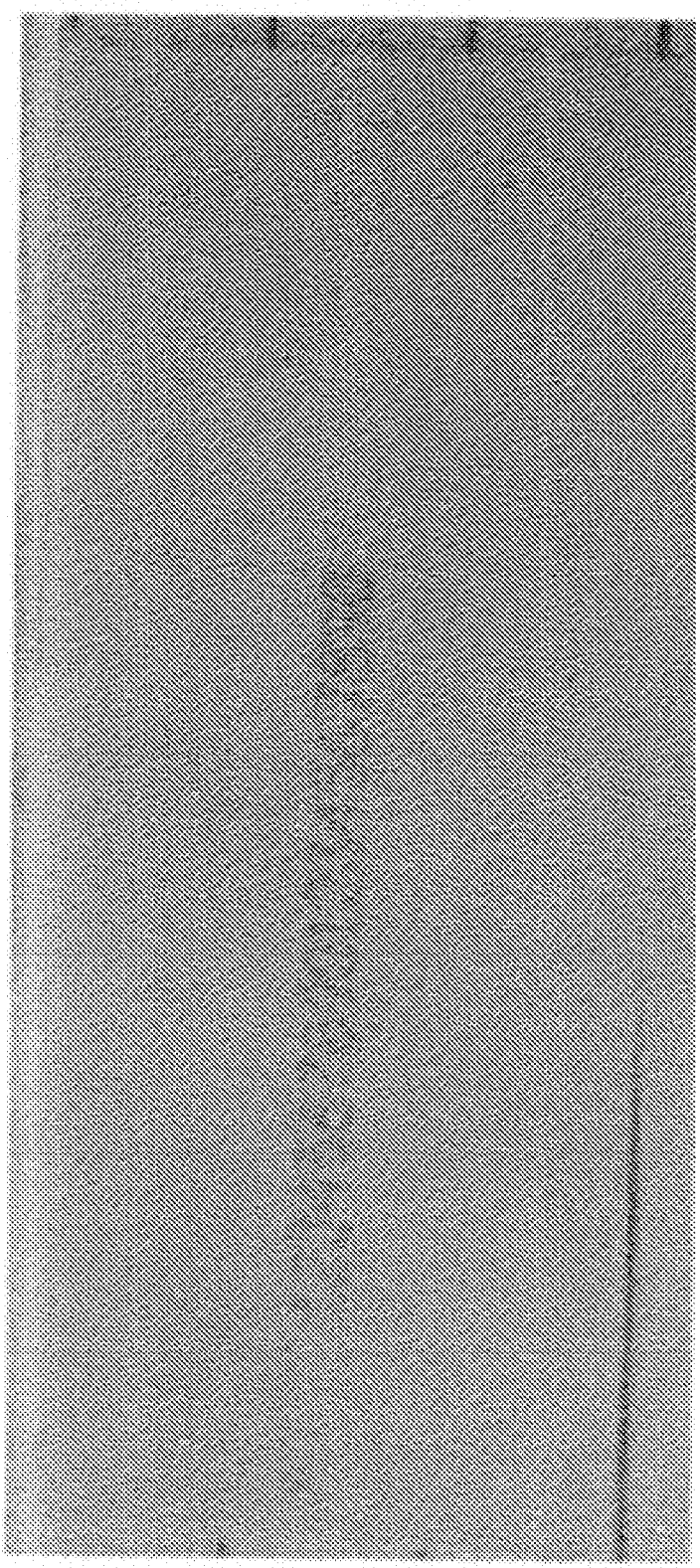

Referring to FIGS. 1 and 2, blank labels were prepared as a polypropylene film facing directed adhered onto an aluminium foil backing. The facing was directly adhered and hence there was no adhesive between the foil and the facing. The first was etched using a UV laser, in a single pass, giving sharp definition of the etched numbering—see FIG. 1. The second was etched with a YAG laser. 3 passes were used to achieve satisfactory definition—see FIG. 2. Both labels were subsequently attached to ampoules using water based acrylic adhesive.

EXAMPLE 2

Figure 3:
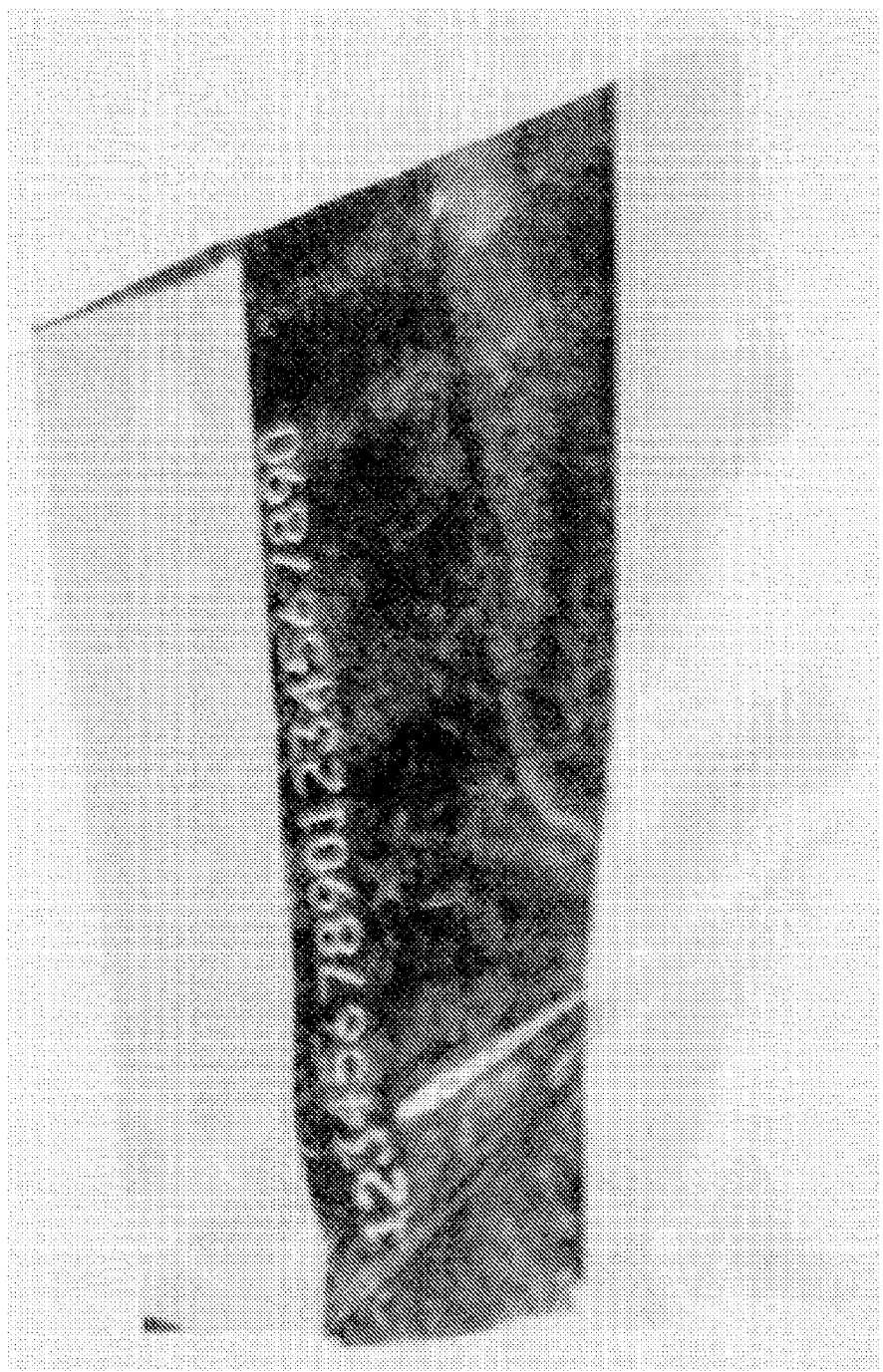
Figure 4:
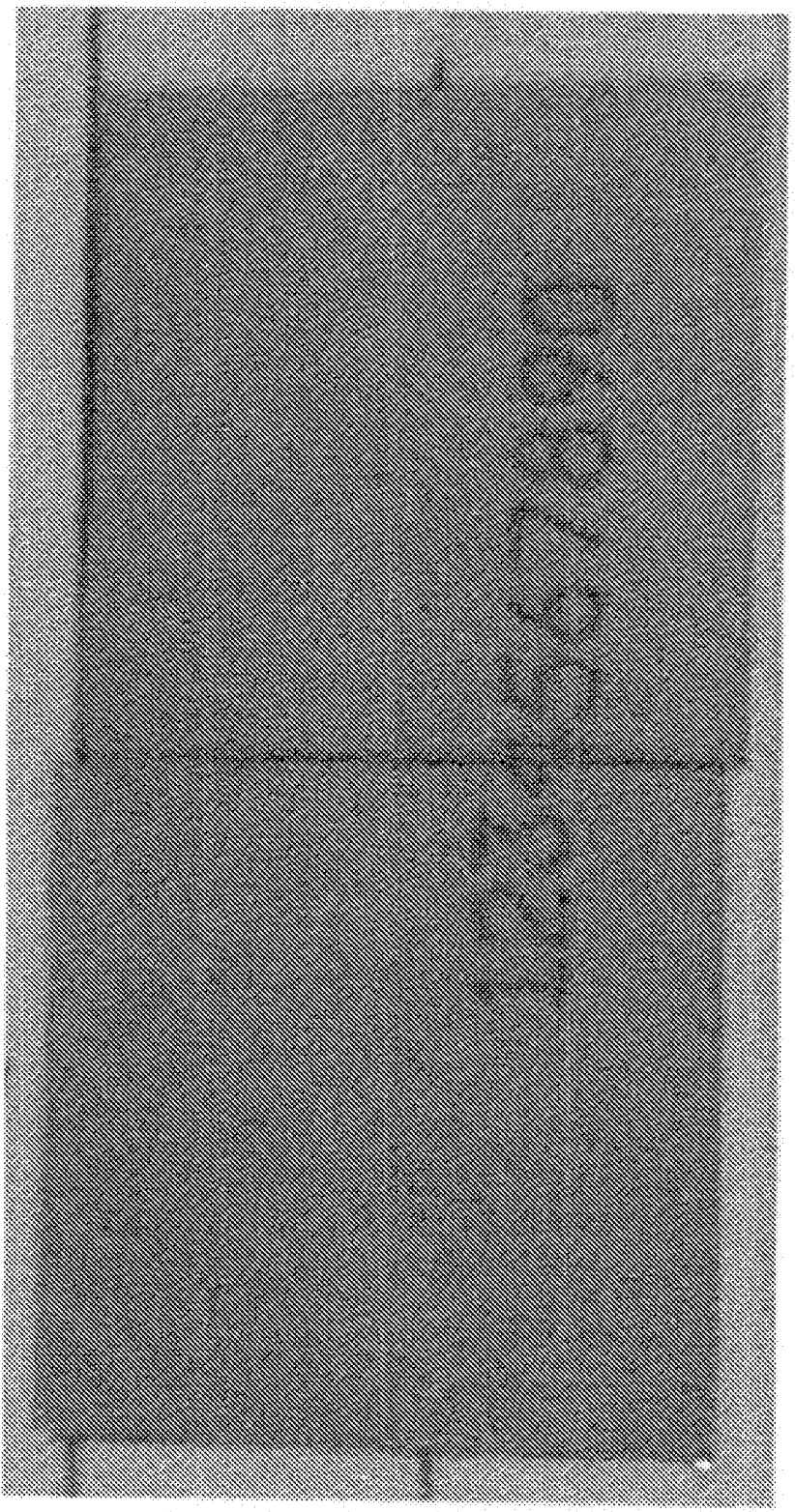

Referring to FIGS. 3 and 4, blank labels were prepared as a sandwich of polyester/aluminium/polypropylene. The first was etched using a UV laser in a single pass, giving sharp definition of the etched numbering—see FIG. 3. The second was etched with a YAG laser, in a single pass, giving satisfactory definition—see FIG. 4. Both types of labels were subsequently attached to ampoules using water based acrylic adhesive.

The invention hence provides labels for ampoules and methods of making these.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:
1. A method of labelling a nebulizer ampoule, the method comprising:
   (i) laser-engraving data on a film comprising a polymer selected from the group consisting of polyester, polypropylene and polyethylene to produce a data film; and
   (ii) affixing the data film onto a nebulizer ampoule using a non-migratory adhesive, wherein (a) the laser-engraving does not produce holes that penetrate the full thickness of the data film and
(b) the method comprises positioning a first intermediate film and a second intermediate film between the data film and the adhesive, wherein the first intermediate film is an aluminum foil, and the second intermediate film comprises a material selected from the group consisting of polyester, polypropylene and polyethylene.

2. The method of claim 1, wherein step (i) is carried out after step (ii).

3. The method of claim 1, wherein step (ii) is carried out after step (i).

4. The method of claim 1, wherein the data film is affixed onto the first intermediate film.

5. The method of claim 1, wherein the first intermediate film or the second intermediate film comprises a metal foil.

6. The method of claim 5, wherein the metal is aluminium.

7. The method of claim 1, wherein the non-migratory adhesive is waterborne and acrylic-based.

8. The method of claim 1, wherein the nebulizer ampoule is made from a material selected from the group consisting of a low density polypropylene and polyethylene by blow-fill-seal or a form-fill-seal method, and the nebulizer ampoule contains no more than 5 ml of medicament.

9. The method of claim 1, wherein the data film does not have any ink.

* * * * *